United States Patent [19]
Gideon

[11] Patent Number: 5,736,144
[45] Date of Patent: Apr. 7, 1998

[54] METHOD OF PRODUCING A MEDICINAL TEA FOR TREATING INFERTILITY IN MALES AND FOR TREATING PROSTATITIS

[76] Inventor: Salva Gideon, 201 Lloyd Manor Road, Suite 200, Etobicoke, Ontario, Canada, M9B 6H6

[21] Appl. No.: 566,498

[22] Filed: Dec. 4, 1995

[30] Foreign Application Priority Data

Dec. 2, 1994 [CA] Canada .................................. 2137219

[51] Int. Cl.$^6$ ...................................................... A01N 65/00
[52] U.S. Cl. ........................ 424/195.1; 424/58; 514/878; 514/931
[58] Field of Search ................................ 424/195.1, 58; 514/878, 931

[56] References Cited

U.S. PATENT DOCUMENTS

| | | |
|---|---|---|
| 4,059,695 | 11/1977 | Hirosaki et al. . |
| 5,009,891 | 4/1991 | Niwa et al. . |
| 5,166,190 | 11/1992 | Mather .......................................... 514/8 |
| 5,250,514 | 10/1993 | Skakkeb ........................................ 514/12 |

FOREIGN PATENT DOCUMENTS

| | | |
|---|---|---|
| 60102161 | 9/1993 | Japan . |
| 61112024 | 9/1993 | Japan . |
| 61239855 | 9/1993 | Japan . |
| 62061570 | 9/1993 | Japan . |
| 62175148 | 9/1993 | Japan . |

OTHER PUBLICATIONS

Sriuastava et al *Nutr Int* 30(4) 1984 907–910 Abstract Only.
Gayal et al *Nutr Rep Int* 30(2) 1984 501–504 Abstract Only.

*Primary Examiner*—Marian C. Knode
*Assistant Examiner*—Heather A. Bakalyar
*Attorney, Agent, or Firm*—Young & Basile, P.C.

[57] ABSTRACT

A medicinal substance for increasing fertility in mammalian males and for use as an anti-microbial or anti-inflammatory agent by mammals produced by boiling radish leaves, radish stems or portions thereof in water for a period of time sufficient to produce a tea containing an extract from the radish leaves and stems or portions thereof. Alternatively, the radish leaves and stems may be placed in hot water for a period of time sufficient to produce a tea containing the extract. The resulting tea can be drunk hot or cold and may be stored in a refrigerator for extended periods of time for later use. Patients taking a daily dosage of this tea have shown greatly improved sperm density and improved motility and morphology after use for several weeks. Dosages of this tea are also effective in treating prostatitis. The preferred radish plant is the spring radish of the species *Raphanus sativus*. The leaves of other radish plants including wild and winter or oriental radishes may also be used.

11 Claims, No Drawings

METHOD OF PRODUCING A MEDICINAL TEA FOR TREATING INFERTILITY IN MALES AND FOR TREATING PROSTATITIS

BACKGROUND OF THE INVENTION

The present invention relates to treatments for treating infertility in males and for treating prostatitis. More particularly, the invention relates to a natural medicine treatment for treating infertility in males who suffer from germinal epithelium failure and for treating prostatitis in males.

For many male and female couples, infertility is an aggravating problem forcing a couple to seek medical attention. The couple's infertility may be caused by the male who may be diagnosed as being infertile or sub-fertile due to poor or insufficient semen quantity and/or quality. Generally, a total sperm count of less than approximately 20 million, with adequate motility and morphology, is considered to be a low sperm count, and males exhibiting such characteristics are considered to be subfertile or oligospermatic. Additionally or alternatively, sperm morphology and motility is another indication of oligospermia, such as when the percentage of abnormal spermatozoa exceeds approximately 40%.

"Germinal epithelium failure" refers to a disorder of mammals that exhibit oligospermia as described above and yet have intact Leydig cell steroidogenic capacity and pituitary cells. Such males have normal testosterone levels but low or non-existent sperm counts. In the former case, the disorder is generally referred to as "partial germinal epithelium failure" while in the latter case, the disorder is generally referred to as "complete germinal epithelium failure". There are various causes for this including genetic tract infections and varicoceles. In addition, the natural aging process may have some effect upon the production of sperm, decreasing in more mature males. However, the largest group of infertile and subfertile men falls into the category of idiopathic oligospermia, without an evident etiology. In these cases, the need for increase in fertility is generally due to a primary testicular disorder, i.e. the cause is not at the hypothalamic or pituitary level.

U.S. Pat. No. 5,166,190 issued Nov. 24, 1992 to Mather et al. and assigned to Genentech, Inc. discloses a method for increasing fertility in a male mammal exhibiting germinal epithelium failure, comprising administering to the mammal, preferably to the testis thereof, an effective amount of activin. Unfortunately, activin is not readily available and must be prepared, such as by being synthesized in a recombinant cell culture as described for example in U.S. Pat. No. 4,798,885 issued Jan. 17, 1989. Hence, activin may be quite an expensive medication to consume. In addition, the necessary dosage of activin is subject to a great deal of therapeutic discretion, with a key factor for selecting an appropriate dosage being the result obtained, as measured by increases in sperm density by semen analysis or the number of spermatocytes, or by. other criteria as deemed appropriate by the practitioner. Such active involvement by the practitioner implies added cost to the treatment of infertility.

U.S. Pat. No. 5,250,514 issued Oct. 5, 1993 to Skakkeb and assigned to Novo Nordisk A/S discloses a method of treating infertility or sub-fertility in adult males. In this method, non-surgically correctable infertility or sub-fertility in adult men having poor semen quality is treated with injections of human Growth Hormone (hGH) in daily doses of 1–10 IU/m$^2$ or in doses in combination with gonadotrophins. Reportedly, increase in total semen volume and total sperm number per ejaculate up to normal figures is obtained for certain males with this treatment. Unfortunately, hGH is a very scarce substance and is therefore very expensive. Furthermore, this treatment is only recommended for men having low levels of hGH and/or demonstrated poor response to conventional infertility treatments.

Conventional treatments include the administration of human chorionic gonadotrophins (hCG), human menopausal gonadotropin (hMG)(consisting of equal amounts of follicle stimulating hormone, FSH, and luteinizing hormone LH), or luteinizing hormone releasing hormone(LHRH), also known as gonadotrophin releasing hormones (GnRH). Treatment with these hormones however, is generally expensive, and generally does not yield satisfactory results for males exhibiting idiopathic oligospermia.

An alternative medicinal treatment to the drugs described above are low cost 'natural' medicines such as various herbs which are typically ingested over large periods of time to form part of one's diet. Two examples Of naturally occurring herbs thought to increase the bodies' production of male hormones include ginseng and sarsaparilla: Bullock S., *Naturally Yours*, Superior Printing, Dallas, Tex., October 1993. Ginseng is derived from any of several plants of the genus Panax, especially *P. pseudoginseng* of eastern Asia or *P. quinquefolius* of North America, typically having small greenish flowers grouped in umbels, palmately compound leaves, and forked roots. Sarsaparilla is derived from any of several tropical American plants of the genus Smilax, or from either of two North American plants (*Aralia hispida* or *A. nudicaulis*), having umbels of small white flowers and bipinnately compound leaves. The roots of these herbs are thought to have the medicinal properties. However, it is inconclusive whether ingestion of these herbs does indeed increase fertility in males exhibiting germinal epithelium failure. Thus any treatment prescribed therewith is conjectural at best.

A fruit thought to aid in sperm production is the pistachio nut, e.g. *Pistacia Vera*. It is believed that pistachio nuts contain proteins which are utilized by the male body in producing sperm. Consequently, pistachio nuts are often "prescribed" to males whenever their body's store of proteins for producing sperm is depleted, such as during periods of frequent sexual activity, and the male's usual level of sperm production is desired. Typically, such frequent sexual activity wherein protein replenishment is desired occurs during an approximately four day period in a woman's ovulation cycle when the chances for conception are most high, and the couple desire to conceive. However, there is no evidence to indicate that pistachio nuts are an effective remedy for males exhibiting germinal epithelium failure in the first instance, as such a disorder involves more than the simple replenishment of proteins.

Due to the very nature of idiopathic oligospermia, an etiology is not diagnosed. Nevertheless, it is often suspected that microbes or other infectious agents may be present within the testes which may act as gonadotoxins. Microbes may also affect other areas of the sexual system such as the prostate. One very common ailment amongst men includes prostatitis, i.e. inflammation/infection of the prostate gland. Antibiotics are usually prescribed for males exhibiting this disorder.

SUMMARY OF THE INVENTION

It is an object of the invention to provide a method of producing a medicinal substance for increasing fertility in males or for treating prostatitis.

It is a further object of the invention to provide a medicinal tea or composition for increasing fertility in males, for use as an anti-microbial agent and/or anti-inflammatory agent, and for treating prostatitis.

In accordance with one aspect of the invention, a method of producing a medicinal substance for increasing fertility in males or an anti-microbial or anti-inflammatory agent for these males comprises boiling a plant material selected from a leafy portion of a radish plant in water for a period of time sufficient to produce a tea from the radish leaves or portions thereof.

According to another aspect of the invention, a method of producing a medicinal tea for increasing fertility in males comprises placing a plant material selected from a leafy portion of a radish plant in hot water for a period of time sufficient to produce a tea from said plant material.

According to further aspects of the invention, there are also provided a composition for increasing fertility in males, a pharmaceutical composition for use as an anti-gonadotoxin, and a medicinal tea for increasing fertility in males, each of which is made by the above-mentioned methods.

According to still another aspect of the invention, a method of treating infertility in a male comprises ingesting into the male an effective amount of leafy portions from radish plants.

According to yet another aspect of the invention, a method for treating microbial infections or inflammations in sexual systems comprises ingesting an effective amount of leafy portions from radish plants.

The radish leaf tea may be appropriately sweetened and ingested hot or cold. Preferably a dosage of one cup of the radish leaf tea is consumed twice daily for a period of at least a few weeks. It has been found that males exhibiting idiopathic oligospermia showed a significant improvement after a few weeks with this treatment, which has the advantage of being readily available, of low cost, and easily administrable. It has also been found that human males exhibiting prostatitis can be effectively treated with this tea made of radish leaves and/or radish stems.

DETAILED DESCRIPTION OF PREFERRED EMBODIMENTS

In one aspect of the invention, a tea from radish leaves is administered to a male exhibiting partial germinal epithelium failure for the treatment thereof. It is important to note that it is the leaves and stem of a radish plant (*Raphanus sativus*) from which a tea is prepared, not the radish root, i.e. not the vegetable itself. The leaves and stems are hereinafter alternatively collectively termed the "leafy portion" of radish plants. Preferably, the leafy portion is obtained from the common, garden variety radish vegetable typically available in most supermarkets and vegetable supply stores across the nation. The preferred radish plant is the species *Raphanus sativus*, an Eurasian plant having a fleshy, edible root and white to purple flowers clustered in a terminal raceme. Any of several different varieties of this plant can be used.

The radish leaves and stems, not the flowers or roots, are clipped from the radish plant and are cleaned by washing with water and the like. For one dosage, preferably the leafy portion of approximately one to three plants are collected, chopped or minced somewhat and boiled in 6–12 ounces of water, Preferably approximately 8–10 ounces of water for a suitable length of time, such as 5–10 minutes, in order to produce a cup of radish leaf tea. Alternatively, the tea may be prepared by steeping the leafy portions in substantially boiling or very hot water for a suitable length of time, e.g. 15 minutes. In either case, it will be appreciated that the scalding water serves to hasten the diffusion and dissolution of the soluble plant material from the leafy portions into the water. The aforesaid amount of radish leaves and stems for the tea is approximately the average amount to be administered to the patient per dosage, although significant variations may be made from the stated amount of radish leaf and stems in boiling water and yet still be effective.

The radish leaf tea may be sweetened appropriately and then ingested by the patient either hot or cold, as desired, to constitute one dosage. As the radish leaf tea may be ingested cold, a large amount of the tea may be prepared at one time and refrigerated in suitable containers for an extended period of time, if desired.

Alternatively, portions of radish leaves and/or stems may be ingested directly without preparing a tea, although the taste is typically not very palatable. When ingested in this manner, the radish leaves can be prepared for instance as a regular salad including assorted salad dressings. It will also be appreciated that the radish plant material containing the active ingredient may be extracted by other methods, such as by a press, and combined with a pharmaceutically acceptable carrier, including water.

In a preferred treatment program, a dosage of the aforesaid radish leaf tea is ingested once or twice daily for a period of at least a few, i.e. four to six, weeks, although the tea may be ingested for a long period of time so as to become almost a daily "ritual". It has been found that a significant improvement in sperm count resulted in males tested for the effects of this treatment:

EXAMPLE 1

A semen analysis was performed on May 12, 1994 in the usual manner, i.e. by collecting a sperm sample after a few days of sexual abstinence, on subject No. 1, a 32 year old male. The analysis indicated a total sperm count of 2.8 million, a motility of 20% and a morphology of 1%, all of which are considered to be abnormal. On Jun. 22, 1994, the subject began drinking one dosage daily of the aforedescribed radish leaf tea. On Jul. 21, 1994, after approximately one month, a semen analysis was again performed on the subject. The analysis showed that the subject produced a sperm density of 5.05 million/ml, a total sperm count of 4 million, with a motility of 50% and a morphology of 60%. The subject continued with the treatment, drinking one cup of tea daily, and on Aug. 23, 1994, about two months since starting the treatment, a semen analysis was again performed. The analysis showed a sperm density of 10.15 million/ml, a total sperm count of 15 million and a motility of 30% (morphology was not quantified). The subject's sperm count improved approximately five-fold in about two months since commencing the treatment of the invention.

EXAMPLE 2

Subject No. 2, a 38 year old, had exhibited oligospermia for a number of years. On Jan. 19, 1993, a semen analysis was performed on the subject which showed a total sperm count of 11.5 million, a motility of 53% and a morphology of 68%. The subject began the radish leaf tea treatment on approximately May 10, 1994, drinking one cup of tea per day. On Jun. 10, 1994 after approximately one month of the treatment, a serum analysis was again performed on the subject. The analysis showed a total sperm count of 20 million and a morphology of 85% (motility was not quantified).

The subject's sperm count improved approximately twofold in about one month since commencing the treatment of the invention.

EXAMPLE 3

Subject No. 3, a 29 year old male, initially suffered from complete germinal epithelium failure. In a semen analysis taken on Mar. 10, 1993, the subject produced a semen sample having a volume of 4.5 ml, but exhibiting a sperm count of zero and a morphology of 0%, i.e. no sperm cells were seen. A semen analysis was again performed on Apr. 1, 1994 which also showed a zero sperm count. A testicular biopsy and semen pathology analysis revealed the presence of early morphological stages of spermatogenesis along with a normal component of Sertoli cells and Leydig cells. The subject was diagnosed as having a subnormal spermatogenic activity referred to as maturation arrest, which was deemed to be irreversible.

The subject began treatment with the radish leaf tea of the present invention on approximately Feb. 10, 1994, drinking one cup of tea daily. On Feb. 21, 1994, after approximately 1.5 weeks of treatment, a semen analysis was performed on the subject. The analysis revealed a sperm density of 8.5 million/ml, a total sperm count of 32.3 million, a 30% motility and a normal morphology, i.e. approximately 80% normal forms. On Mar. 25, 1994, after approximately six weeks since commencing the treatment, a semen analysis performed on the subject showed a sperm density of 28.6 million/ml, a total sperm count of approximately 105 million, a motility of approximately 55% and a normal morphology. A further semen analysis taken on Jun. 30, 1994 revealed a sperm density of 37.1 million/ml, a total sperm count of approximately 148 million, a motility of 55% and a normal morphology. On Nov. 9, 1994 the subject's partner determined that she had become pregnant. The subject was apparently off the treatment for one month before conception.

It should be appreciated from the above examples that a significant improvement in sperm count should result, on average, in approximately four to six weeks. Of course, significant variations in improvement per individual are likely to occur depending on factors such as genetic disposition, diet, age, abnormal stress, etc.

While in the discussion above reference has been made specifically to human males, it is believed that the aforesaid radish leaf treatment for germinal epithelium failure will be effective in substantially most mammalian males. Naturally herbivorous mammals can ingest the radish leaf in its natural state, without necessarily having to prepare the tea. Furthermore, the amount of radish leaf required to be ingested in order to produce a noticeable effect will vary significantly depending upon the type, size and weight of the mammal.

While not wishing to be bound by any one theory, it is hypothesized that the radish leaf tea includes an active ingredient which acts as an anti-gonadotoxin that kills any bacteria or the like interfering with the maturation of sperm, thereby providing a healthy sperm-producing environment in the testis. As an indication of the anti-gonadotoxin effect of the radish leaf tea, a decrease in white cell count was noticed in certain samples of the subjects above.

The theory that the radish leaf tea acts generally as an anti-microbial agent with respect to male reproductive organs is further buttressed by the following additional example wherein a subject was successfully treated for prostatitis:

EXAMPLE 4

On May 15, 1991, a semen analysis test was performed on subject No. 4, then a 29 year old male. The subject showed an excellent sperm count of 230 million/cc with 95 % motility and a normal morphology. However, the patient's white blood cell count was 24–25/hpf. The subject was subsequently referred to an urologist who, on Jun. 25, 1991, diagnosed the subject as having a low grade chronic asymptomatic prostatitis. The subject was prescribed with an antibiotic, Bactrim DS 1 bid, for six weeks.

Unfortunately, prostatitis was a recurring problem with the subject. A Jul. 28, 1994 semen analysis showed that the subject had a normal sperm count of 158 million/cc with a 95% motility and a normal morphology, however, the subject had a leucocytes count of greater than 50/hpf, which is indicative of prostatitis.

The subject thereafter began the radish leaf tea treatment of one cup per day for one month only. On Nov. 10, 1994 a semen analysis test was again performed on the subject. This time, the results showed a normal sperm count of 237 million/cc with normal motility and morphology, but with a very low white cell count, i.e. in the order of 0–2 white cells/HPF.

Thus, the evidence has disclosed that the radish leaf tea can act as an anti-microbial/anti inflammatory agent, particularly for the condition of prostatitis.

The anti-microbial or anti-inflammatory type of effect and anti-gonadotoxin effect of this tea may be used for women with pelvic inflammatory disease and women with repeat miscarriages. Drinking this tea a few times a month may prevent infections or inflammations in women using an IUD as a contraceptive and this can prevent ectopic pregnancies.

Although the leaves of spring radishes (*Raphanus sativus*) were used in the above examples, the leaves of winter or oriental radishes (*R-sativus vat. longipinnatus*) could also be used. The leaves of wild radishes, a variety of the garden or spring radish, may also be used for the above described purposes. Wild and garden radishes are considered by some botanists as two varieties of the species Raphanus raphanistrum. The Black Spanish Radish (*Raphanus sativus var-major*) may be used as well.

It will be appreciated by persons skilled in the art that the present invention is not limited by what has been particularly described herein. Rather, the scope of the present invention is defined only by the claims which follow.

I therefore claim:

1. A method of treating clinically diagnosed infertility in a mammalian male comprising:
   (a) boiling the leafy portions of radish plants of the species *Raphanus sativus* in water for a period of time sufficient to produce a tea, and
   (b) having said male ingest tea produced by the method of step (a) in a treatment program comprising prescribed dosages of said tea for an ongoing treatment sufficient to restore the fertility of said male.

2. The method of claim 1 wherein the prescribed dosages of said tea consist of the leafy portions of 1 to 3 said radish plants boiled in 6 to 12 ounces of water.

3. The method of claim 1 or 2 wherein multiple dosages of tea are prepared by producing a single amount of tea at one time and portioning single dosages of tea into containers.

4. A method of treating microbial infections or inflammations in the sexual organs of a mammalian male comprising:
   (a) boiling the leafy portions of radish plants of the species *Raphanus sativus* in water for a period of time sufficient to produce a tea, and
   (b) having said male ingest tea produced by the method of step (a) in a treatment program comprising prescribed dosages of said tea for an ongoing treatment sufficient to treat said microbial infections or inflammation in the sexual organs of said male.

5. The method of claim 4 wherein the prescribed dosages of said tea consist of the leafy portions of 1 to 3 said radish plants boiled in 6 to 12 ounces of water.

6. The method of claim 4 wherein said microbial infections or inflammations in the sexual organs of a male results in prostatitis.

7. The method of claim 4, 5 or 6 wherein multiple dosages of tea are prepared by producing a single amount of tea at one time and portioning single dosages of tea into containers.

8. A method of treating clinically diagnosed infertility in a mammalian male comprising:
 (a) pressing the leafy portions of radish plants of the species *Raphanus sativus* to produce an extract, and
 (b) having said male ingest extract produced by the method of step (a) in a treatment program comprising prescribed dosages of said extract for an ongoing treatment sufficient to restore the fertility of said male.

9. A method of treating microbial infections or inflammations in the sexual organs of a mammalian male comprising:
 (a) pressing the leafy portions of radish plants of the species *Raphanus sativus* to produce an extract, and
 (b) having said male ingest extract produced by the method of step (a) in a treatment program comprising prescribed dosages of said extract for an ongoing treatment sufficient to treat said microbial infections or inflammation in the sexual organs of said male.

10. The method of claim 9 wherein said microbial infections or inflammations in the sexual organs of a male results in prostatitis.

11. The method of claim 1, 4, 8 or 9 wherein the radish plants of the species *Raphanus sativus* are selected from the group consisting of *Raphanus sativus vat. Major* and *Raphanus sativus var. Longipinnatus*.

* * * * *